US012605099B2

(12) United States Patent
Kim et al.

(10) Patent No.: US 12,605,099 B2
(45) Date of Patent: Apr. 21, 2026

(54) NEURAL ELECTRODE FOR MEASURING NEURAL SIGNAL AND METHOD FOR MANUFACTURING THE SAME

(71) Applicant: ELECTRONICS AND TELECOMMUNICATIONS RESEARCH INSTITUTE, Daejeon (KR)

(72) Inventors: Yong Hee Kim, Daejeon (KR); Sang Don Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 309 days.

(21) Appl. No.: 18/443,144

(22) Filed: Feb. 15, 2024

(65) Prior Publication Data

US 2024/0407698 A1    Dec. 12, 2024

(30) Foreign Application Priority Data

Jun. 7, 2023    (KR) ........................ 10-2023-0072778

(51) Int. Cl.
| | |
|---|---|
| *A61B 5/294* | (2021.01) |
| *A61B 5/263* | (2021.01) |
| *C25D 7/00* | (2006.01) |

(52) U.S. Cl.
CPC .............. *A61B 5/294* (2021.01); *A61B 5/263* (2021.01); *A61B 2562/0285* (2013.01); *A61B 2562/125* (2013.01); *C25D 7/006* (2013.01)

(58) Field of Classification Search
CPC . A61B 5/294; A61B 5/263; A61B 2562/0285; A61B 2562/125; C25D 7/006
See application file for complete search history.

(56) References Cited

U.S. PATENT DOCUMENTS

| | | |
|---|---|---|
| 9,650,720 B2 | 5/2017 | Kim et al. |
| 11,278,713 B2 | 3/2022 | Kim et al. |
| | (Continued) | |

FOREIGN PATENT DOCUMENTS

| | | |
|---|---|---|
| KR | 10-2014-0043236 A | 4/2014 |
| KR | 10-2015-0095964 A | 8/2015 |
| KR | 10-2016-0107527 A | 9/2016 |

OTHER PUBLICATIONS

Yong Hee Kim et al., "In vitro extracellular recording and stimulation performance of nanoporous gold-modified multi-electrode arrays," J Neural Eng., 2015.

(Continued)

*Primary Examiner* — Linda C Dvorak
*Assistant Examiner* — William Mossbrook

(57) ABSTRACT

Disclosed are a neural electrode for measuring a neural signal and a method for manufacturing the same. The method includes forming a bottom electrode on a substrate, forming a passivation layer exposing a portion of the bottom electrode, forming a metal layer including a gold nano-structure and a silver nano-structure on the bottom electrode, selectively forming the gold nano-structure having porosity by selectively removing the silver nano-structure, forming lower nano-particles on an inner sidewall of the gold nano-structure, and forming an upper nano-coating layer on the lower nano-particles and the inner sidewall of the gold nano-structure.

16 Claims, 10 Drawing Sheets

(56) References Cited

U.S. PATENT DOCUMENTS

| | | |
|---|---|---|
| 2013/0153113 A1 | 6/2013 | Lee et al. |
| 2014/0020936 A1* | 1/2014 | Kim .......................... H05K 3/10 |
| | | 174/255 |
| 2015/0112180 A1* | 4/2015 | Kim ....................... A61B 5/291 |
| | | 600/377 |
| 2018/0345005 A1* | 12/2018 | Kim .......................... A61B 5/24 |
| 2019/0076038 A1 | 3/2019 | Kim et al. |
| 2019/0187135 A1 | 6/2019 | Kim et al. |

OTHER PUBLICATIONS

Yong Hee Kim et al., "Iridium Oxide—Electrodeposited Nanoporous Gold Multielectrode Array with Enhanced Stimulus Efficacy," Nano Lett., 2016.

* cited by examiner

NEURAL ELECTRODE FOR MEASURING NEURAL SIGNAL AND METHOD FOR MANUFACTURING THE SAME

CROSS-REFERENCE TO RELATED APPLICATION

This U.S. non-provisional patent application claims priority under 35 U.S.C. § 119 of Korean Patent Application No. 10-2023-0072778, filed on Jun. 7, 2023, the entire contents of which are hereby incorporated by reference.

BACKGROUND

The present disclosure herein relates to a neural electrode for measuring a neural signal and a method for manufacturing the same.

In the field of in-vivo or in-vitro neural interfaces for recording neural signals from nerve cells, researches are carried out to develop materials for improving the performance of neural electrodes.

First-generation neural electrodes made of wires of metal such as platinum, gold, tungsten, or iridium and second-generation neural electrodes made of semiconductors or multi-arrays have been developed, and researches are carried out to develop third-generation neural electrodes surface-modified with nano-structures.

It is necessary to record a neural signal for each nerve cell in order to more accurately detect a neural condition, and, to this end, the size of an electrode is decreased to the size (about 10 μm) of a nerve cell.

SUMMARY

The present disclosure provides a neural electrode surface modifying method for reducing impedance of a neural electrode and improving charge storage capacity and charge injection limit performance by increasing inner/outer surface areas of a typical nano-porous structure.

An embodiment of the inventive concept provides a method for manufacturing a neural electrode, the method including: forming a bottom electrode on a substrate; forming a passivation layer exposing a portion of the bottom electrode; forming a metal layer including a gold nano-structure and a silver nano-structure on the bottom electrode; selectively forming the gold nano-structure having porosity by selectively removing the silver nano-structure; forming lower nano-particles on an inner sidewall of the gold nano-structure; and forming an upper nano-coating layer on the lower nano-particles and the inner sidewall of the gold nano-structure.

In an embodiment, the forming of the lower nano-particles may include electro-depositing gold nano-particles.

In an embodiment, the gold nano-structure may have surface area density higher than surface area density of the gold nano-particles.

In an embodiment, the forming of the upper nano-coating layer may include electro-depositing an iridium nano-particle layer.

In an embodiment, the upper nano-coating layer may have surface area density higher than the surface area density of the gold nano-particles.

In an embodiment, density of the gold nano-structure may be higher than density of the upper nano-coating layer.

In an embodiment, the method may further include forming a groove by removing a portion of the gold nano-structure exposed by the lower nano-particles.

In an embodiment, the upper nano-coating layer may be formed in the groove.

In an embodiment, the substrate may include transparent glass.

In an embodiment, the passivation layer may include a silicon oxide.

In an embodiment of the inventive concept, a neural electrode for measuring a neural signal includes: a bottom electrode on a substrate; a passivation layer covering both edges of the bottom electrode; a gold nano-structure having porosity and provided on the bottom electrode exposed from the passivation layer; lower nano-particles provided on an inner sidewall of the gold nano-structure; and an upper nano-coating layer provided on the lower nano-particles and the inner sidewall of the gold nano-structure. In an embodiment, the lower nano-particles may contact a sidewall of the gold nano-structure to increase a surface area of the upper nano-coating layer.

In an embodiment, the gold nano-structure may have a groove provided between the lower nano-particles.

In an embodiment, the groove may have a V-shaped cross section.

In an embodiment, the gold nano-structure may have surface area density higher than surface area density of the lower nano-particles.

In an embodiment, the upper nano-coating layer may have surface area density higher than surface area density of the lower nano-particles.

In an embodiment, density of the gold nano-structure may be higher than density of the upper nano-coating layer.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
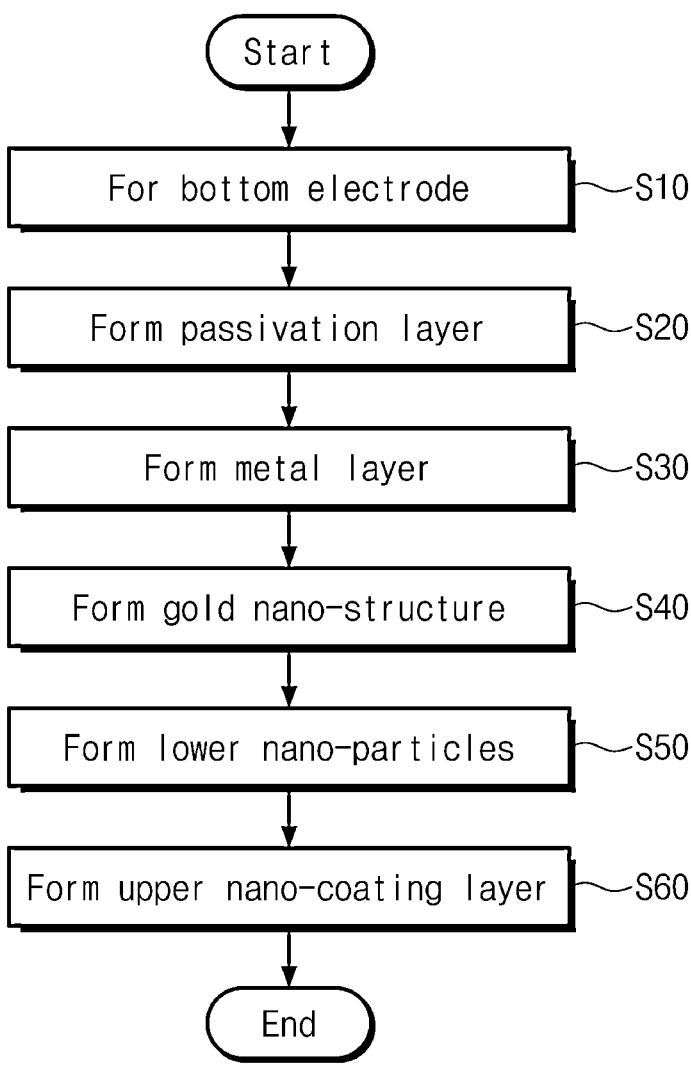
FIG. 1 is a flowchart illustrating a method for manufacturing a neural electrode for measuring a neural signal according to an embodiment of the inventive concept.

Embodiments of the inventive concept will now be described in detail with reference to the accompanying drawings. Advantages and features of embodiments of the inventive concept, and methods for achieving the advantages and features will be apparent from the embodiments described in detail below with reference to the accompanying drawings. However, the inventive concept may be embodied in different forms and should not be construed as limited to the embodiments set forth herein. Rather, these embodiments are provided so that this disclosure will be thorough and complete, and will fully convey the scope of the inventive concept to those skilled in the art, and the inventive concept is only defined by the scope of the claims. Like reference numerals refer to like elements throughout.

The terminology used herein is not for delimiting the embodiments of the inventive concept but for describing the embodiments of the inventive concept. The terms of a singular form may include plural forms unless otherwise specified. The term "include," "comprise," "including" or "comprising" specifies an element, a step, an operation and/or an element but does not exclude other elements, steps, operations and/or elements. Furthermore, reference numerals, which are presented in the order of description, are provided according to the embodiments and are thus not necessarily limited to the order. In addition, in this description, when a certain film is referred to as being on another film or substrate, it can be directly on the other film or substrate, or a third film may be interposed therebetween.

The embodiments of the inventive concept will be described with reference to example cross-sectional views and/or plan views. In the drawings, the dimensions of layers and regions are exaggerated for clarity of illustration. Therefore, the forms of the example drawings may be changed due to a manufacturing technology and/or error tolerance. Therefore, the embodiments of the inventive concept may involve changes of shapes depending on a manufacturing process, without being limited to the illustrated specific forms. For example, a curved fluid and polymer layer may be formed flat. Therefore, the regions illustrated in the drawings are merely schematic, and the shapes of the regions exemplify specific shapes of the elements but do not limit the scope of the invention.

FIG. 1 illustrates an example of a method for manufacturing a neural electrode for measuring a neural signal according to the inventive concept. FIGS. 2 to 6 are cross-sectional views illustrating a method for manufacturing a neural electrode for measuring a neural signal.

Figure 2:
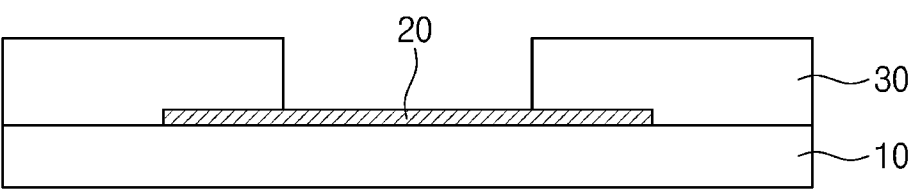
FIGS. 2 to 6 are cross-sectional views illustrating a method for manufacturing a neural electrode for measuring a neural signal.

Referring to FIGS. 1 and 2, a bottom electrode 20 is formed on a substrate 10 (S10). The substrate 10 may include transparent glass or transparent quartz. Alternatively, the substrate 10 may include a flexible substrate, but an embodiment of the inventive concept is not limited thereto. The bottom electrode 20 may be formed using a sputtering method, a photolithography method, and an etching method. The bottom electrode 20 may include gold, but an embodiment of the inventive concept is not limited thereto.

Next, a passivation layer 30 is formed on both edges of the bottom electrodes 20 (S20). The passivation layer 30 may include an insulator of a silicon oxide film. The passivation layer 30 may be formed using a chemical vapor deposition method and an etching method. Alternatively, the passivation layer 30 may include a polymer of perfluoropolyetherurethane acrylate (PFPEUA), but an embodiment of the inventive concept is not limited thereto.

FIGS. 7 to 10 illustrate examples of a metal layer 40, a gold nano-structure 42, lower nano-particles 46, and an upper nano-coating layer 48 that are formed on the bottom electrode 20 of FIG. 2.

Figure 3:
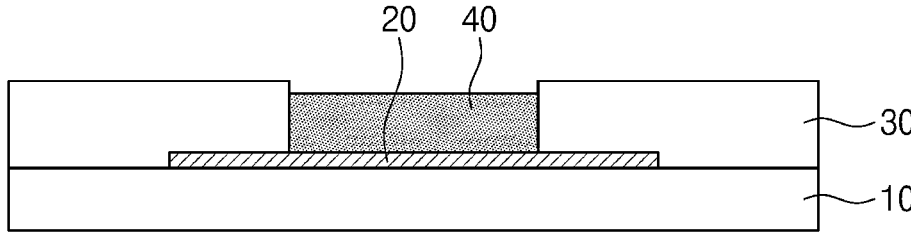
Figure 7:
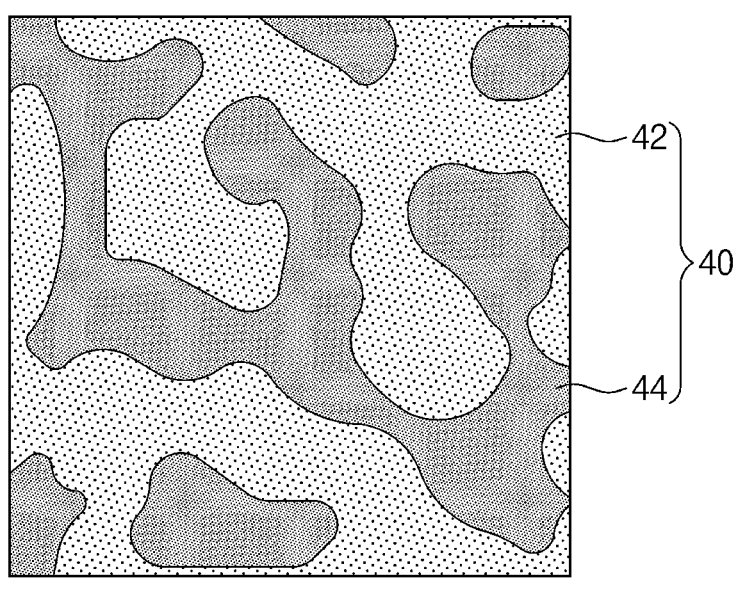
FIGS. 7 to 10 are diagrams illustrating examples of the metal layer, the gold nano-structure, the lower nano-particles, and the upper nano-coating layer that are formed on the bottom electrode of FIG. 2.

Referring to FIGS. 1, 3, and 7, the metal layer 40 is formed on a center of the bottom electrode 20 (S30). According to an example, the metal layer 40 may include a gold nano-structure 42 and a sliver nano-structure 44. The gold nano-structure 42 and the silver nano-structure 44 may have a one-to-one mixture ratio. The gold nano-structure 42 and the silver nano-structure 44 may be formed through an electrodeposition process.

Figure 4:
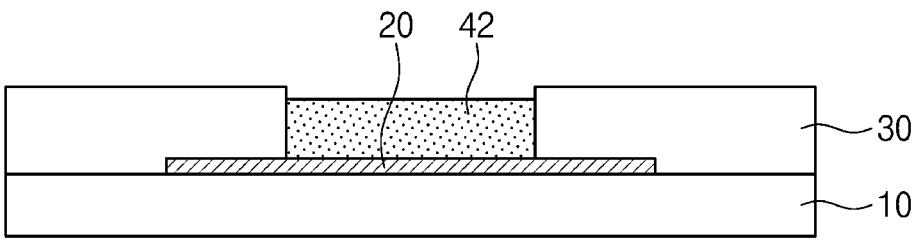
Figure 8:
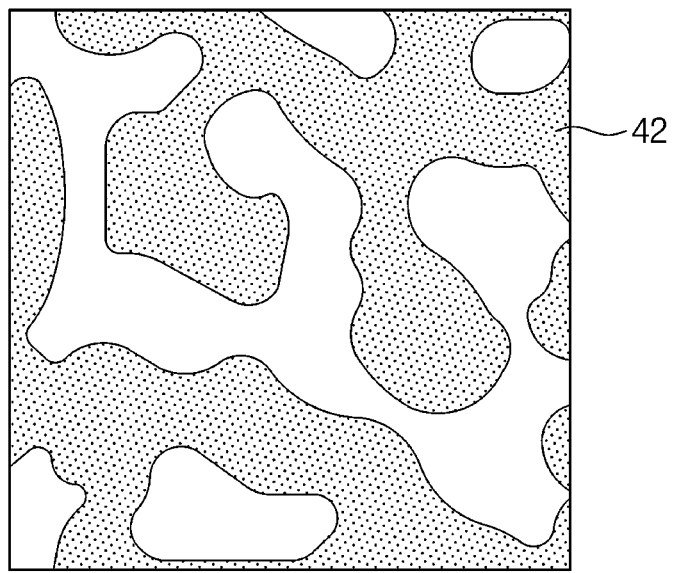

Referring to FIGS. 1, 4, and 8, the gold nano-structure 42 is selectively formed by removing the silver nano-structure 44 of the metal layer 40 (S40). The silver nano-structure 44 may be selectively removed when the substrate 10 is immersed in a nitric acid solution. The gold nano-structure 42 may remain on the bottom electrode 20 due to an etching process of the silver nano-structure 44. A removal time of the silver nano-structure 44 may be determined by a thickness of the metal layer 40 and a temperature of the nitric acid solution. When the metal layer 40 has a thickness of about 500 nm and the nitric acid solution has a temperature of about 70° C., the silver nano-structure 44 may be removed for about 15 minutes. Since the silver nano-structure 44 in the gold nano-structure 42 has toxicity, the silver nano-structure 44 is required to be removed for a sufficient time.

Figure 5:
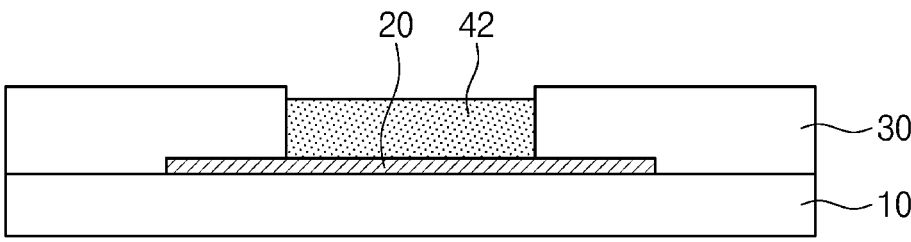
Figure 9:
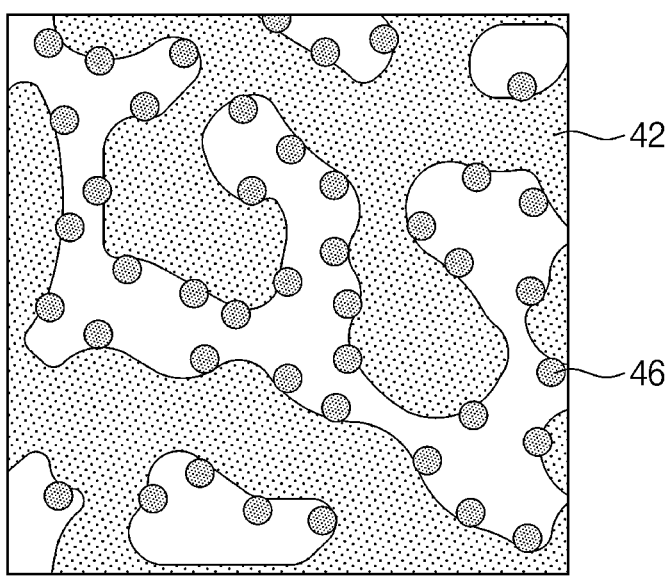

Referring to FIGS. 1, 5, and 9, the lower nano-particles 46 are formed on an inner sidewall of the gold nano-structure 42 (S50). The lower nano-particles 46 may be formed through an electrodeposition process. The lower nano-particles 46 may be formed on the gold nano-structure 42. According to an example, the lower nano-particles 46 may have a surface area density lower than a surface area density of the gold nano-structure 42. The lower nano-particles 46 may include gold nano-particles. Alternatively, the lower nano-particles 46 may include platinum nano-particles or tungsten nano-particles, but an embodiment of the inventive concept is not limited thereto.

Figure 6:
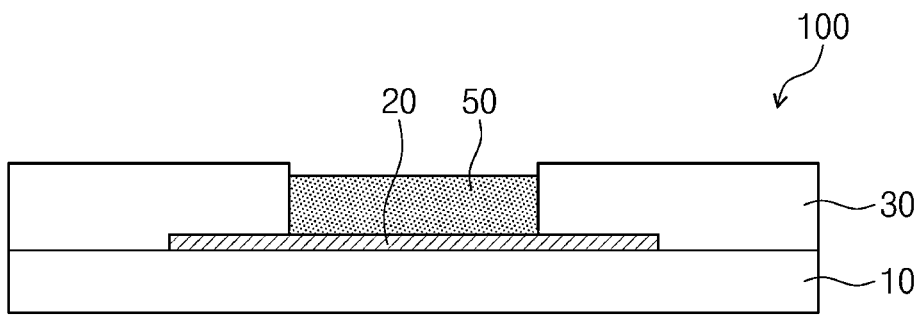
Figure 10:
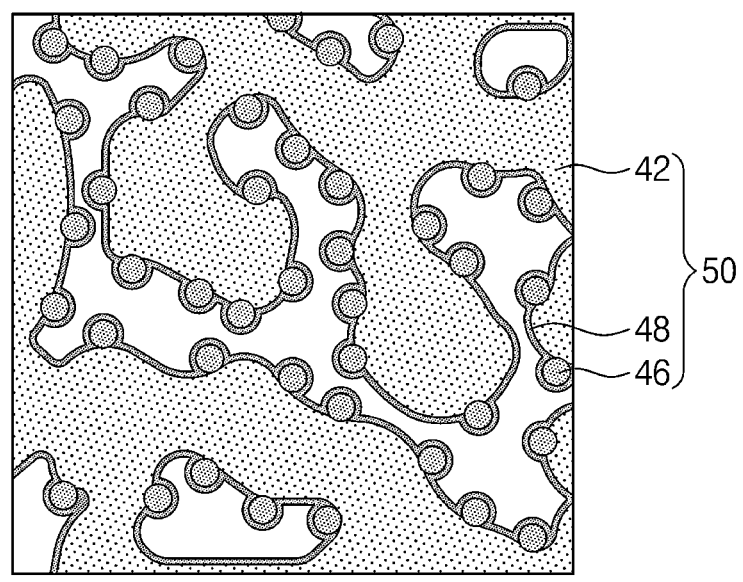

Referring to FIGS. 1, 6, and 10, the upper nano-coating layer 48 are formed on an inner sidewall of the gold nano-structure 42 and the lower nano-particles 46, and a forming process of a neural electrode 50 is completed (S60). The upper nano-coating layer 48 may include an iridium oxide or iridium nano-particle layer formed through an electrodeposition process. The upper nano-coating layer 48 may have a density lower than a density of the gold nano-structure 42 and higher than a density of the lower nano-particles 46.

The lower nano-particles 46 may be provided between the gold nano-structure 42 and the upper nano-coating layer 48, thus increasing a surface area of the upper nano-coating layer 48. Therefore, electrical characteristics of the neural electrode 50 may increase.

Figure 11:
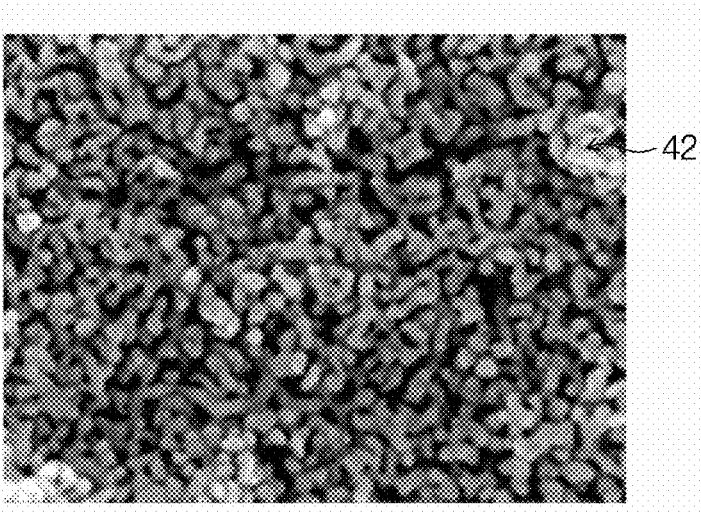
FIGS. 11 and 12 are electron micrographs illustrating examples of the gold nano-structure of FIG. 8 and the neural electrode of FIG. 10.
Figure 12:
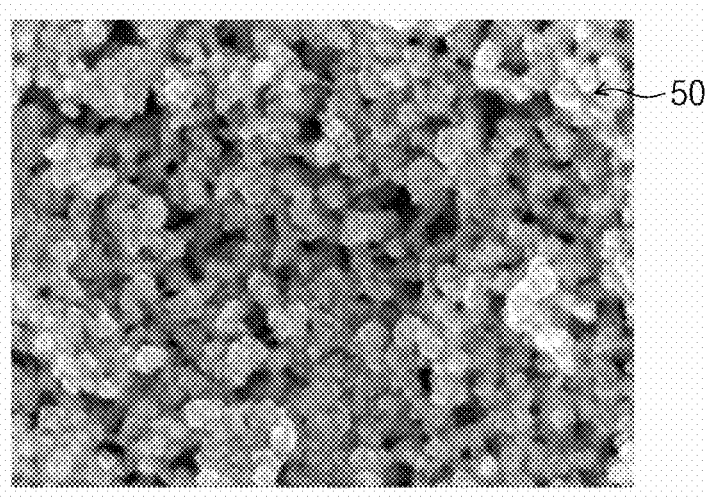

FIGS. 11 and 12 illustrate examples of the gold nano-structure 42 of FIG. 8 and the neural electrode 50 of FIG. 10.

Referring to FIGS. 10 to 12, the neural electrode 50 may have increased surface roughness due to the lower nano-particles 46 on the gold nano-structure 42.

Figure 13:
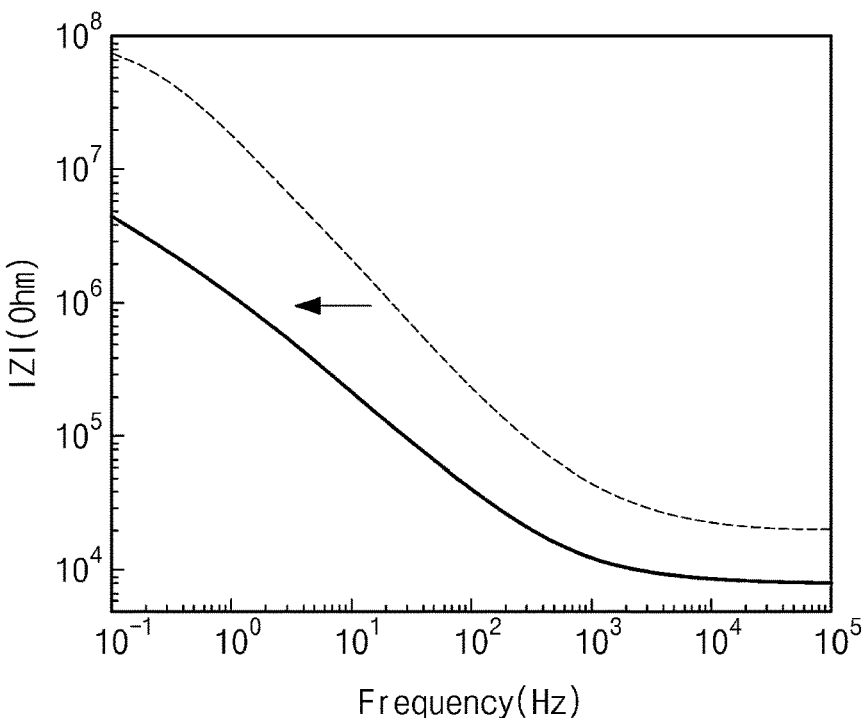
FIGS. 13 and 14 are graphs showing the results of electrochemical impedance spectroscopic measurement and current density-voltage measurement on the neural electrode of FIG. 10.
Figure 14:
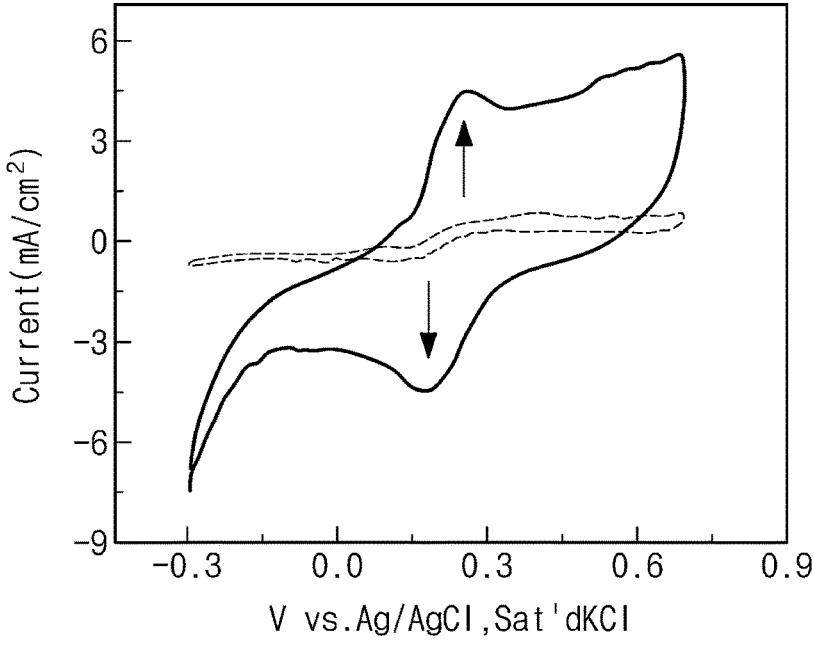

FIGS. 13 and 14 show results of electrochemical impedance spectroscopic measurement and current density-voltage measurement on the neural electrode 50 of FIG. 10.

Referring to FIG. 13, since the lower nano-particles 46 are electro-deposited on the gold nano-structure 42, impedance may reduce in the direction of the arrow in an entire frequency domain.

Referring to FIG. 14, since the lower nano-particles 46 are electro-deposited on the gold nano-structure 42, charge storage capacity may significantly increase in the direction of the arrow.

From these measurement results, it may be inferred that the lower nano-particles 46 may significantly increase a surface area of the porous gold nano-structure 42.

Electro-depositing the upper nano-coating layer 48 on surfaces of the lower nano-particles 46 electro-deposited on the gold nano-structure 42 may cause an additional reduction and increase in the electrochemical impedance and charge storage capacity.

Figure 15:
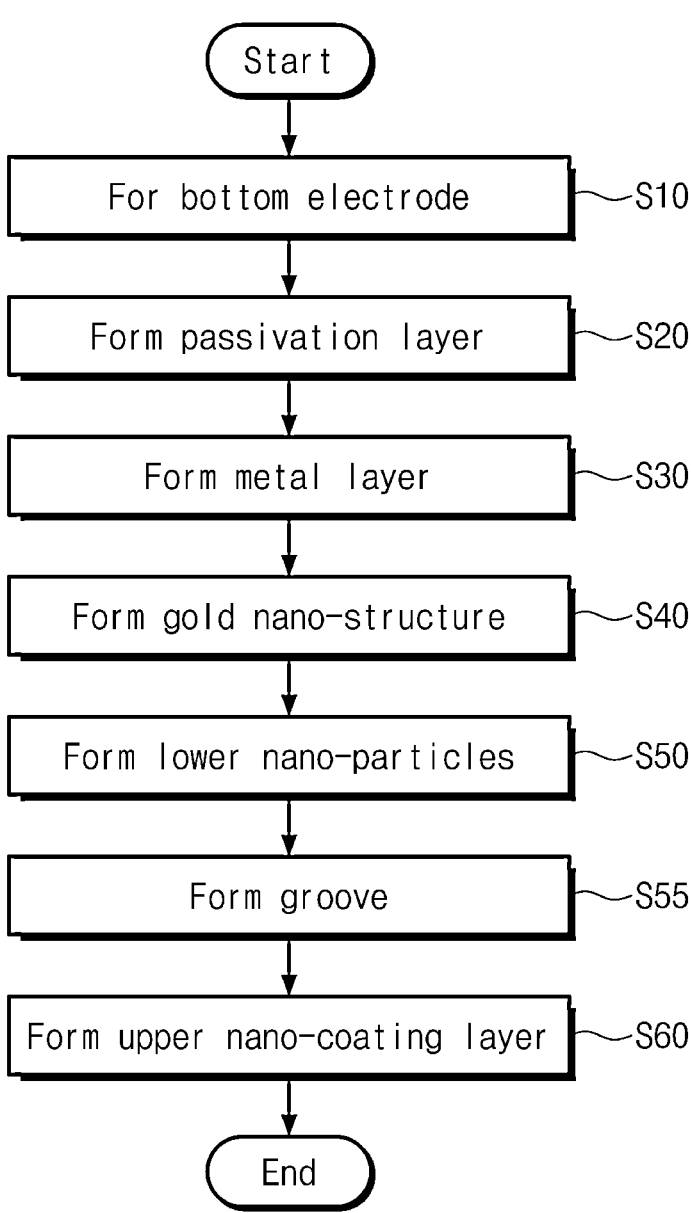
FIG. 15 is a flowchart illustrating an example of a method for manufacturing a neural electrode for measuring a neural signal according to the inventive concept.

FIG. 15 illustrates an example of a method for manufacturing a neural electrode for measuring a neural signal according to the inventive concept. FIGS. 16 to 19 illustrate examples of the metal layer 40, the gold nano-structure 42, the lower nano-particles 46, and the upper nano-coating layer 48 that are formed on the bottom electrode 20 of FIG. 2.

Referring to FIGS. 15 to 19, the method for manufacturing a neural electrode for measuring a neural signal of the inventive concept may further include a step (S55) of forming a groove 47.

Figure 16:
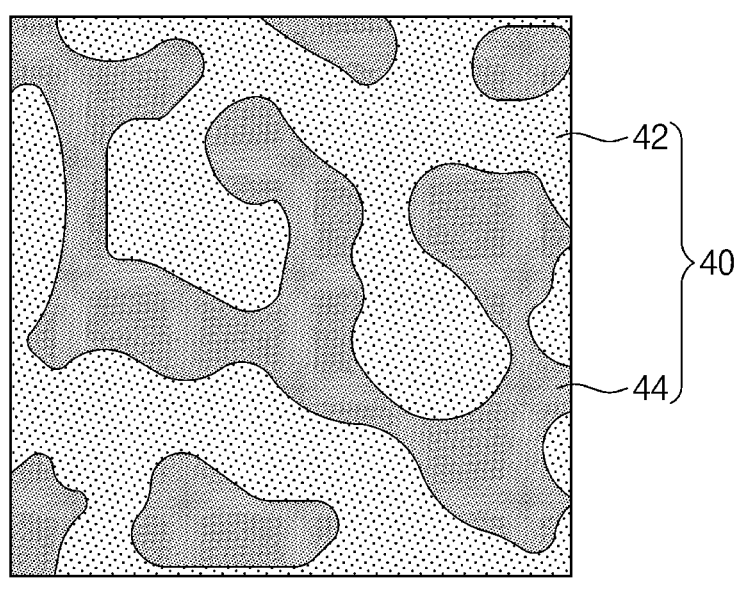
FIGS. 16 to 19 are diagrams illustrating examples of the metal layer, the gold nano-structure, the lower nano-particles, and the upper nano-coating layer that are formed on the bottom electrode of FIG. 2.
Figure 17:
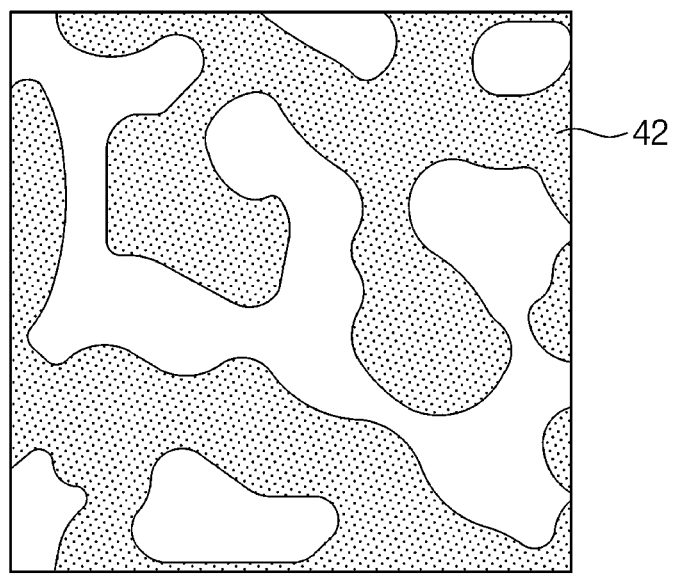

Referring to FIGS. 15 to 17, the gold nano-structure 42 may be formed to have porosity through an etching process of the silver nano-structure 44. The lower nano-particles 46 may be formed on an inner sidewall of the gold nano-structure 42 through an electrodeposition process of gold nano-particles, platinum nano-particles, or tungsten nano-particles.

Figure 18:
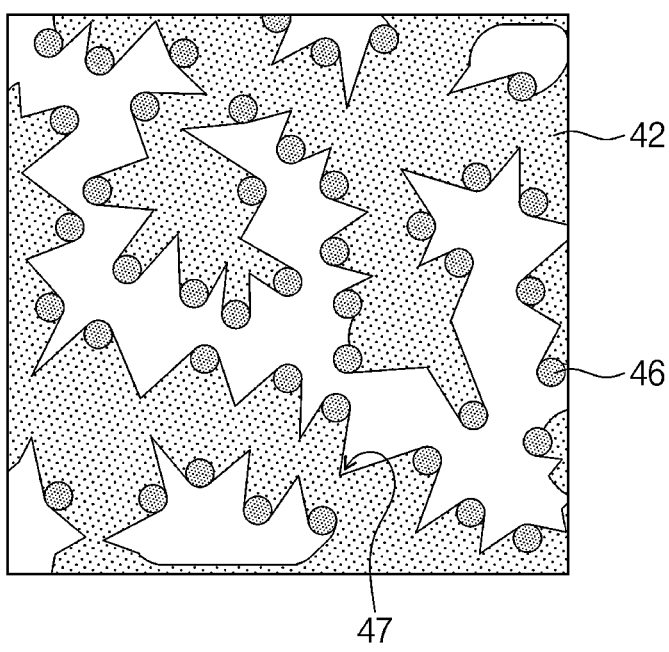

Referring to FIG. 18, the groove 47 may be formed through an etching process of the gold nano-structure 42 exposed by the lower nano-particles 46. The etching process may include a wet etching process using an acid solution as an etchant. The gold nano-structure 42 may have etch selectivity with respect to the lower nano-particles 46. The lower nano-particles 46 and the gold nano-particles 42 may include different types of metals. The lower nano-particles 46 may include platinum nano-particles or tungsten nano-particles.

Figure 19:
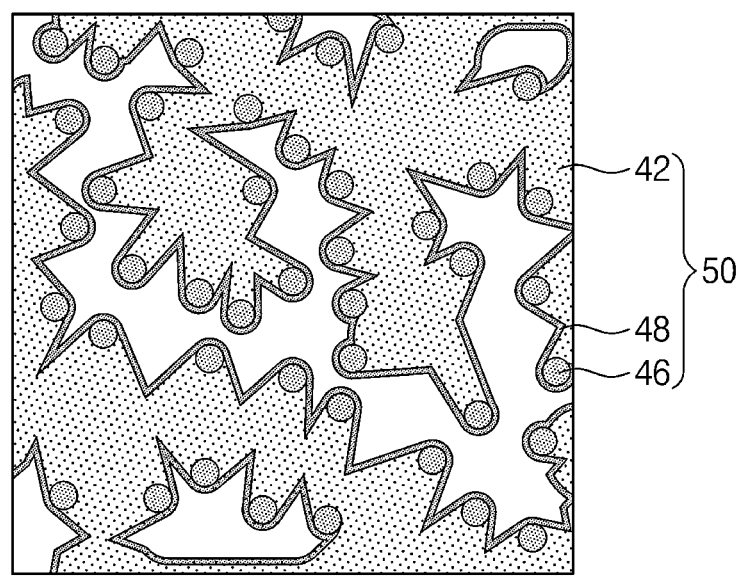

Referring to FIG. 19, the upper nano-coating layer 48 may be formed on the lower nano-particles 46 and in the groove 47. The upper nano-coating layer 48 may include an iridium oxide.

A step S10 of forming the bottom electrode 20, a step S20 of forming the passivation layer 30, a step S30 of forming the metal layer 40, a step S40 of forming the metal nano-structure 42, a step S50 of forming the lower nano-particles 46, and a step S60 of forming the upper nano-coating layer 48 may be configured in the same manner as illustrated in FIGS. 1 to 6.

As described above, a method for manufacturing a neural electrode according to an embodiment of the inventive concept may increase the surface area of an iridium nano-coating layer by suing a nano-particle layer on an inner sidewall of a porous structure.

Although the embodiments of the present invention have been described, it is understood that the present invention should not be limited to these embodiments but various changes and modifications can be made by one ordinary skilled in the art within the spirit and scope of the present invention as hereinafter claimed.

What is claimed is:

1. A method for manufacturing a neural electrode, the method comprising:
forming a bottom electrode on a substrate;
forming a passivation layer exposing a portion of the bottom electrode;
forming a metal layer including a gold nano-structure and a silver nano-structure on the bottom electrode;
selectively forming the gold nano-structure having porosity by selectively removing the silver nano-structure;
forming lower nano-particles on an inner sidewall of the gold nano-structure; and
forming an upper nano-coating layer on the lower nano-particles and the inner sidewall of the gold nano-structure.

2. The method of claim 1, wherein the substrate includes transparent glass.

3. The method of claim 1, wherein the passivation layer includes a silicon oxide.

4. The method of claim 1, further comprising forming a groove by removing a portion of the gold nano-structure exposed by the lower nano-particles.

5. The method of claim 4, wherein the upper nano-coating layer is formed in the groove.

6. The method of claim 1, wherein the forming of the lower nano-particles includes electro-depositing gold nano-particles.

7. The method of claim 6, wherein the gold nano-structure has surface area density higher than surface area density of the gold nano-particles.

8. The method of claim 7, wherein the forming of the upper nano-coating layer includes electro-depositing an iridium nano-particle layer.

9. The method of claim 8, wherein the upper nano-coating layer has surface area density higher than the surface area density of the gold nano-particles.

10. The method of claim 9, wherein density of the gold nano-structure is higher than density of the upper nano-coating layer.

11. A neural electrode for measuring a neural signal, the neural electrode comprising:
a bottom electrode on a substrate;
a passivation layer covering both edges of the bottom electrode;
a gold nano-structure having porosity and provided on the bottom electrode exposed from the passivation layer;
lower nano-particles provided on an inner sidewall of the gold nano-structure; and
an upper nano-coating layer provided on the lower nano-particles and the inner sidewall of the gold nano-structure,
wherein the lower nano-particles contact a sidewall of the gold nano-structure to increase a surface area of the upper nano-coating layer.

12. The neural electrode of claim 11, wherein the gold nano-structure has a groove provided between the lower nano-particles.

13. The neural electrode of claim 12, wherein the groove has a V-shaped cross section.

14. The neural electrode of claim 11, wherein the gold nano-structure has surface area density higher than surface area density of the lower nano-particles.

15. The neural electrode of claim 14, wherein the upper nano-coating layer has surface area density higher than surface area density of the lower nano-particles.

16. The neural electrode of claim 15, wherein density of the gold nano-structure is higher than density of the upper nano-coating layer.

* * * * *